(12) United States Patent
Kamada et al.

(10) Patent No.: US 12,257,047 B2
(45) Date of Patent: Mar. 25, 2025

(54) CONCENTRATION MEASUREMENT DEVICE AND CONCENTRATION MEASUREMENT METHOD

(71) Applicant: HAMAMATSU PHOTONICS K.K., Hamamatsu (JP)

(72) Inventors: Tsuyoshi Kamada, Hamamatsu (JP); Takeo Ozaki, Hamamatsu (JP); Wataru Kamo, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 921 days.

(21) Appl. No.: 17/293,061

(22) PCT Filed: Oct. 30, 2019

(86) PCT No.: PCT/JP2019/042666
§ 371 (c)(1),
(2) Date: May 12, 2021

(87) PCT Pub. No.: WO2020/121675
PCT Pub. Date: Jun. 18, 2020

(65) Prior Publication Data
US 2021/0401335 A1 Dec. 30, 2021

(30) Foreign Application Priority Data
Dec. 10, 2018 (JP) .................. 2018-230876

(51) Int. Cl.
*A61B 5/1455* (2006.01)
*A61B 5/00* (2006.01)
*A61B 5/08* (2006.01)

(52) U.S. Cl.
CPC ........ *A61B 5/14551* (2013.01); *A61B 5/0816* (2013.01); *A61B 5/7225* (2013.01); *A61B 5/742* (2013.01)

(58) Field of Classification Search
CPC . A61B 5/1455; A61B 5/14551; A61B 5/7225; A61B 5/742
See application file for complete search history.

(56) References Cited

U.S. PATENT DOCUMENTS

2004/0122300 A1 6/2004 Boas et al.
2011/0046462 A1 2/2011 Ono et al.
(Continued)

FOREIGN PATENT DOCUMENTS

JP H05-245129 A 9/1993
JP 2004-008572 A 1/2004
(Continued)

OTHER PUBLICATIONS

International Preliminary Report on Patentability mailed Jun. 24, 2021 for PCT/JP2019/042666.

*Primary Examiner* — Eric F Winakur
(74) *Attorney, Agent, or Firm* — Faegre Drinker Biddle & Reath LLP

(57) ABSTRACT

A concentration measurement apparatus includes a light input unit for inputting measurement light to a measurement target portion, a light detection unit for detecting the measurement light propagated inside the measurement target portion, and generating a detection signal according to an intensity of the measurement light, and a calculation unit for obtaining hemoglobin-related information based on the detection signal. The calculation unit performs filter processing of extracting a component derived from respiration among frequency components included in the detection signal, the hemoglobin-related information, or a numerical value appearing in a calculation process of the hemoglobin-related information for obtaining the hemoglobin-related information in a vein of the measurement target portion.

4 Claims, 15 Drawing Sheets

(56) References Cited

U.S. PATENT DOCUMENTS

2013/0066174 A1 3/2013 Addison et al.
2014/0323874 A1 10/2014 Addison et al.
2016/0354011 A1 12/2016 Stahl
2017/0188919 A1 7/2017 Al-Ali et al.

FOREIGN PATENT DOCUMENTS

| JP | 2013-170881 A | 9/2013 |
| JP | 2014-155639 A | 8/2014 |
| WO | WO-2017/040178 A1 | 3/2017 |
| WO | WO 2018/051832 A1 | 3/2018 |

Fig.7
(a)
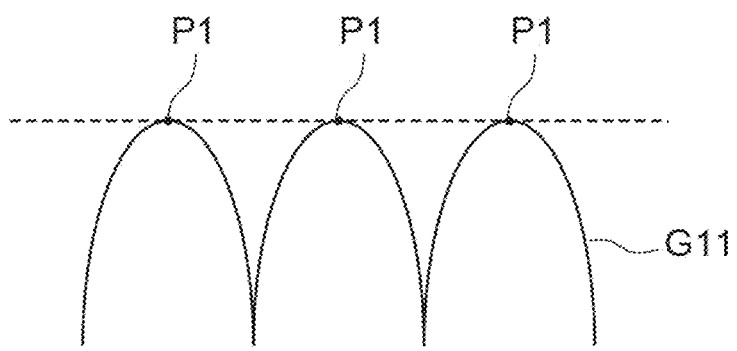
(b)
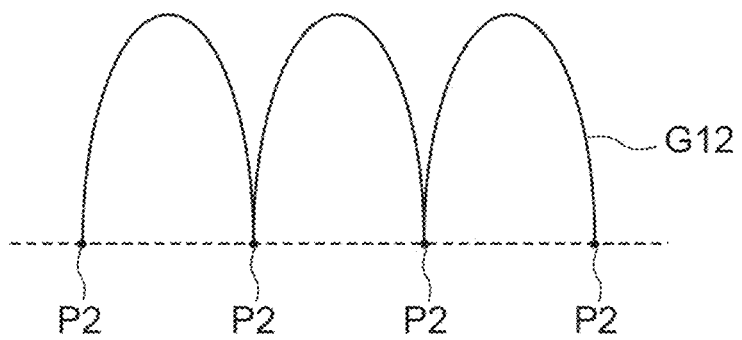

Fig.15
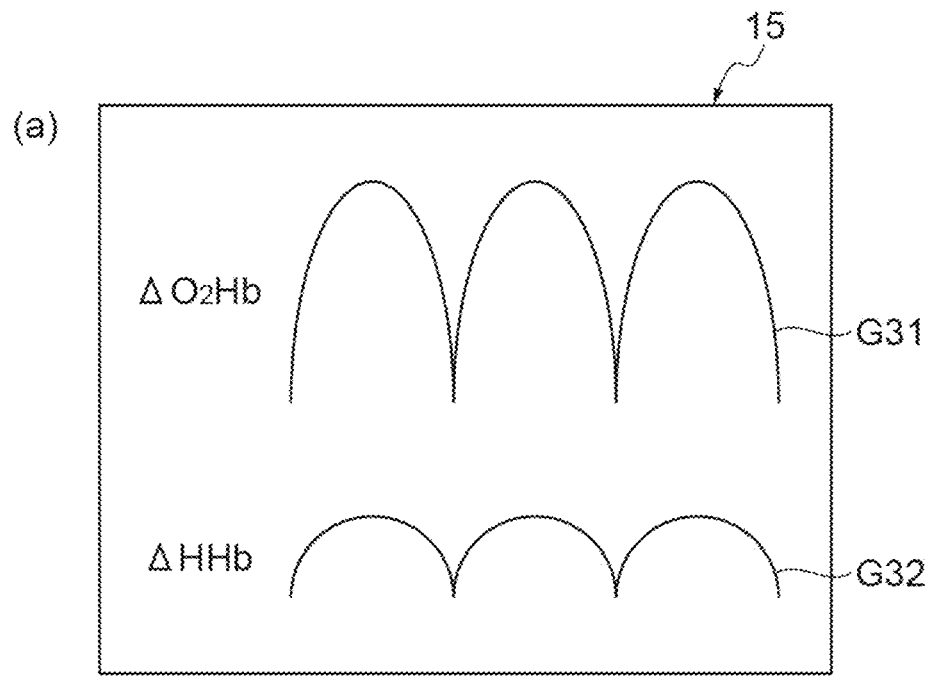
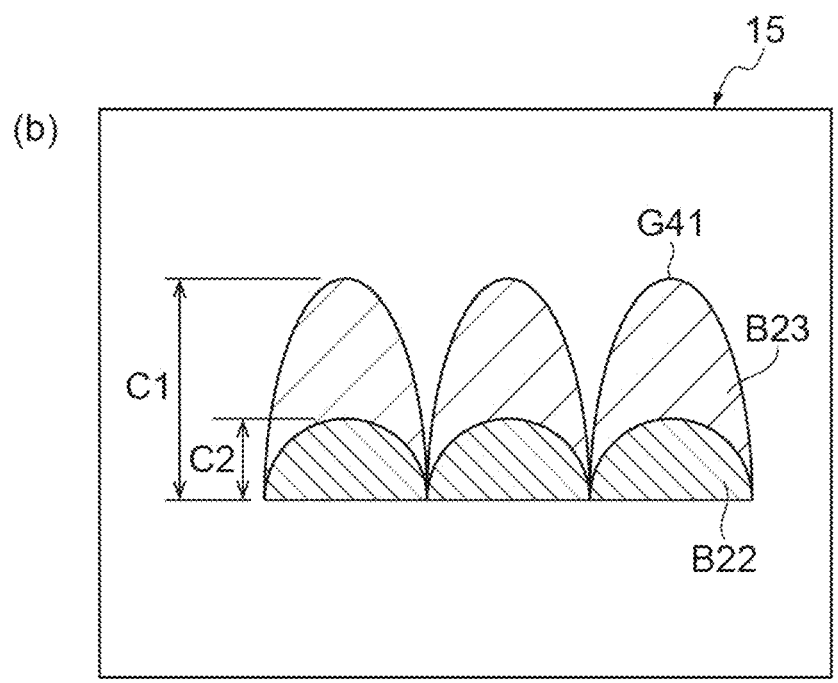

CONCENTRATION MEASUREMENT DEVICE AND CONCENTRATION MEASUREMENT METHOD

TECHNICAL FIELD

The present disclosure relates to a concentration measurement apparatus and a concentration measurement method.

BACKGROUND ART

Patent Document 1 discloses a technique relating to an apparatus and a method for non-invasively measuring hemoglobin concentration information in a living body. The apparatus disclosed in this document includes a light input unit that inputs measurement light to a head, a light detection unit that detects the measurement light propagated inside the head and generates a detection signal according to an intensity of the measurement light, and a CPU that obtains a temporal relative change amount of a oxygenated hemoglobin concentration and performs filter processing that removes frequency components smaller than a predetermined frequency from frequency components included in the relative change amount. The CPU determines the presence or absence of chest compression.

CITATION LIST

Patent Literature

Patent Document 1: Japanese Patent Application Laid-Open Publication No. 2013-170881

SUMMARY OF INVENTION

Technical Problem

A method and an apparatus for measuring hemoglobin-related information such as a hemoglobin oxygen saturation in a living body using light are known. In these method and apparatus, since the entire measurement target portion is irradiated with light, the hemoglobin-related information of an entire tissue including arteries and veins in the measurement target portion is obtained. However, for example, when an oxygen consumption in the measurement target portion is measured, it is necessary to obtain the hemoglobin-related information of veins.

Conventionally, it is difficult to selectively obtain hemoglobin-related information of a vein by a method using light, and it is necessary to use an invasive method such as indwelling a catheter in the vein. In such a method, burden and risk of a subject are high, and it is particularly difficult to apply the method to a newborn and a child. Further, measurement data is likely to vary depending on the direction or the indwelling state of the catheter in a blood vessel, and there is also a problem in measurement stability.

An object of an embodiment is to provide a concentration measurement apparatus and a concentration measurement method capable of non-invasively obtaining hemoglobin-related information of a vein by using light.

Solution to Problem

An embodiment is a concentration measurement apparatus. The concentration measurement apparatus includes a light input unit for inputting measurement light to a measurement target portion; a light detection unit for detecting the measurement light propagated inside the measurement target portion, and generating a detection signal according to an intensity of the measurement light; and a calculation unit for obtaining hemoglobin-related information including at least one of a temporal relative change amount of a total hemoglobin concentration, a temporal relative change amount of an oxygenated hemoglobin concentration, a temporal relative change amount of a deoxygenated hemoglobin concentration, and a hemoglobin oxygen saturation based on the detection signal, and the calculation unit performs filter processing of extracting a component derived from respiration among frequency components included in the detection signal, the hemoglobin-related information, or a numerical value appearing in a calculation process of the hemoglobin-related information for obtaining the hemoglobin-related information in a vein of the measurement target portion.

An embodiment is a concentration measurement method. The concentration measurement method includes a light input step of inputting measurement light to a measurement target portion; a light detection step of detecting the measurement light propagated inside the measurement target portion, and generating a detection signal according to an intensity of the measurement light; and a calculation step of obtaining hemoglobin-related information including at least one of a temporal relative change amount of a total hemoglobin concentration, a temporal relative change amount of an oxygenated hemoglobin concentration, a temporal relative change amount of a deoxygenated hemoglobin concentration, and a hemoglobin oxygen saturation based on the detection signal, and in the calculation step, filter processing of extracting a component derived from respiration among frequency components included in the detection signal, the hemoglobin-related information, or a numerical value appearing in a calculation process of the hemoglobin-related information is performed for obtaining the hemoglobin-related information in a vein of the measurement target portion.

Advantageous Effects of Invention

According to the concentration measurement apparatus and the concentration measurement method of the embodiments, hemoglobin-related information of a vein can be non-invasively obtained using light.

BRIEF DESCRIPTION OF DRAWINGS

FIG. 7 includes (a), (b) diagrams for explaining a concept of filter processing.

FIG. 15 includes (a), (b) diagrams of examples of a display screen in a display unit.

DESCRIPTION OF EMBODIMENTS

Hereinafter, embodiments of a concentration measurement apparatus and a concentration measurement method will be described in detail with reference to the accompanying drawings. In the description of the drawings, the same elements will be denoted by the same reference signs, and redundant description will be omitted.

Figure 1:
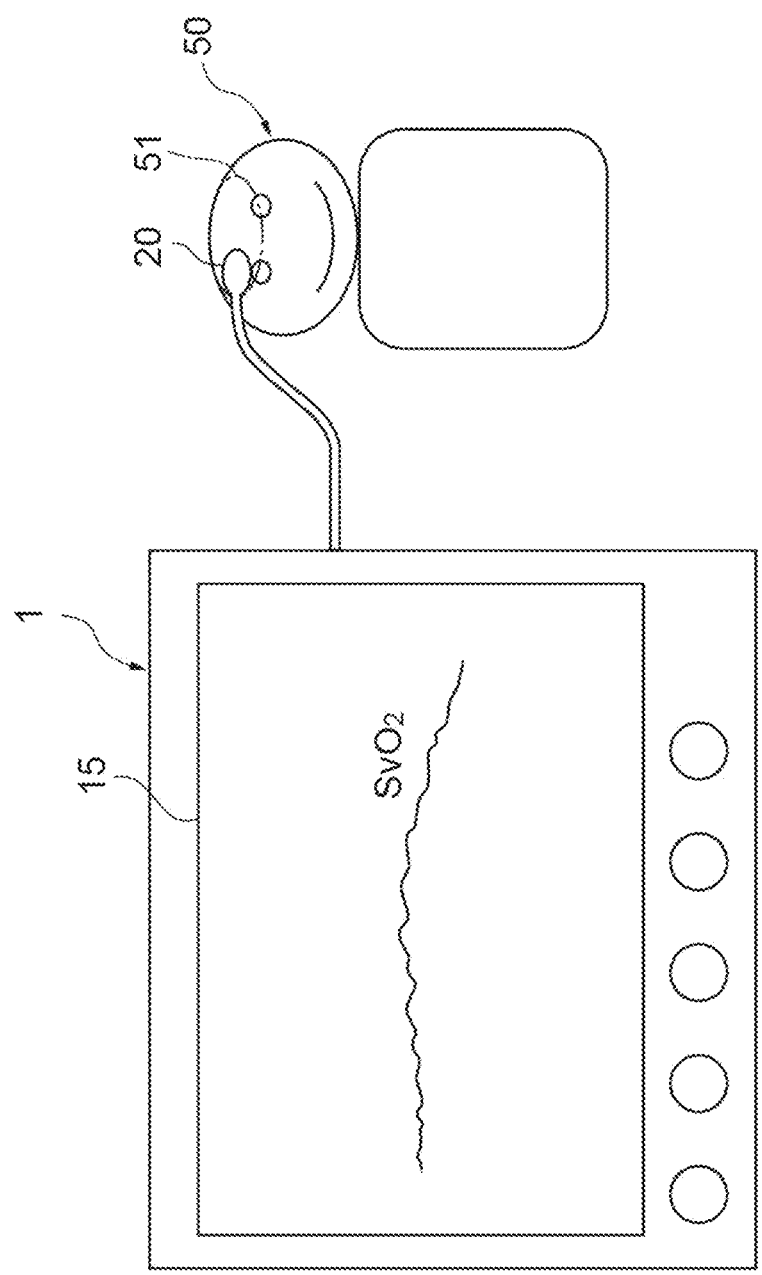
FIG. 1 is a conceptual diagram of a concentration measurement apparatus according to an embodiment.

FIG. 1 is a conceptual diagram of a concentration measurement apparatus 1 according to an embodiment. The concentration measurement apparatus 1 measures hemoglobin-related information of a vein in a measurement target portion 51 of a subject 50, displays it on a display unit 15 to present it to the subject 50 or a measurer. The measurement target portion 51 is, for example, a portion above a neck, specifically, a head (in particular, an intracranial portion of a top of head, a front of head, a forehead, a back of head, a side of head, or the like) and/or a vicinity of a face (ear, nose, eyelid, mouth circumference, jaw, cheek, or the like).

Further, the hemoglobin-related information includes at least one of a temporal relative change amount ($\Delta O_2Hb$) from an initial amount of an oxygenated hemoglobin concentration, a temporal relative change amount ($\Delta HHb$) from an initial amount of a deoxygenated hemoglobin concentration, a temporal relative change amount ($\Delta cHb$) from an initial amount of a total hemoglobin concentration being the sum of these, and a hemoglobin oxygen saturation ($SvO_2$) calculated from $\Delta O_2Hb$ and $\Delta HHb$.

The concentration measurement apparatus 1 inputs light of predetermined wavelengths ($\lambda_1$, $\lambda_2$, $\lambda_3$) to a light input position from a probe 20 fixed to the measurement target portion 51, detects an intensity of light output from a light detection position in the measurement target portion 51, and examines an influence of oxygenated hemoglobin and deoxygenated hemoglobin on the light and repeatedly calculates the hemoglobin-related information based on the results. Further, when the hemoglobin-related information is calculated, the concentration measurement apparatus 1 performs filter processing on a detection signal related to a light intensity, the hemoglobin-related information, or a numerical value appearing in a calculation process of the hemoglobin-related information, and extracts a component derived from respiration among frequency components included therein. Then, the hemoglobin-related information of the vein is obtained based on the frequency component, and the information is visually displayed. In addition, for example, near-infrared light is used as the light of the predetermined wavelength.

Figure 2:
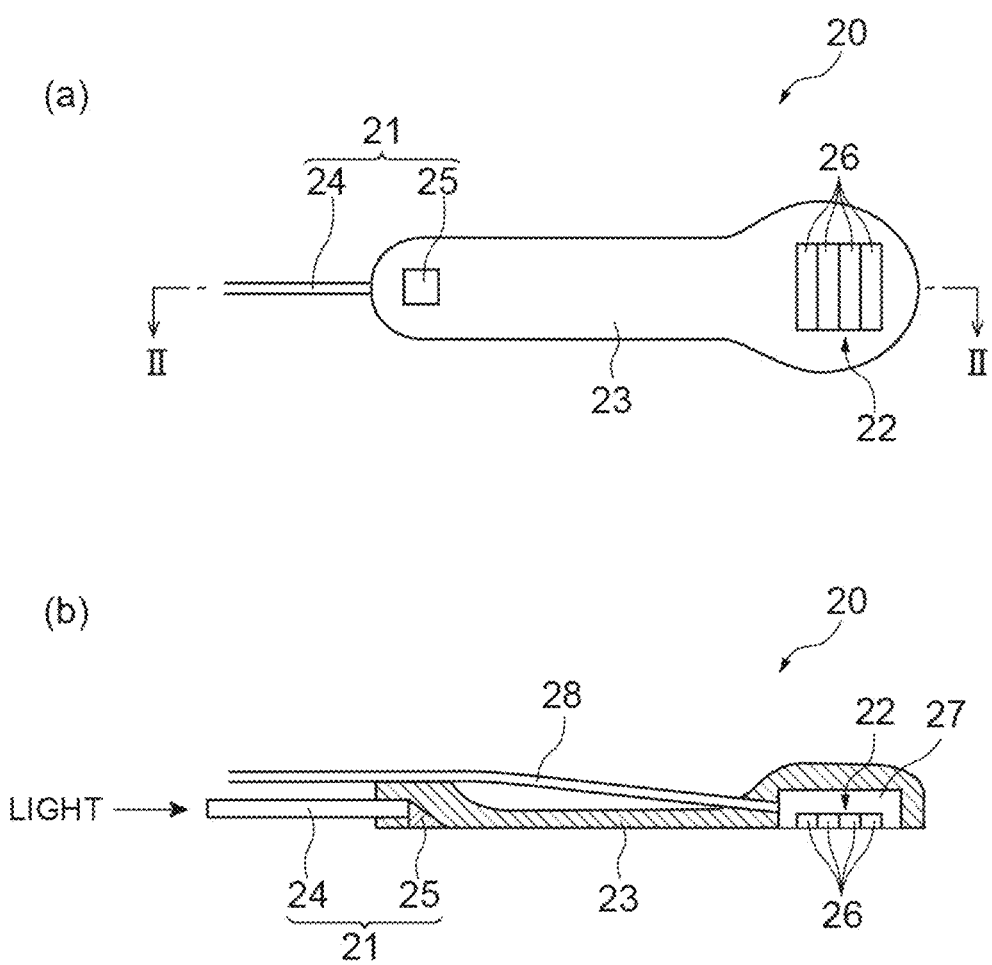
FIG. 2 includes (a) a plan view illustrating a configuration of a probe, and (b) a side cross-sectional view taken along a line II-II in (a).

(a) in FIG. 2 is a plan view illustrating a configuration of the probe 20. Further, (b) in FIG. 2 is a side cross-sectional view taken along a line II-II in (a) in FIG. 2. The probe 20 includes a light input unit 21 and a light detection unit 22. The light input unit 21 and the light detection unit 22 are arranged at an interval of, for example, 5 cm from each other, and are substantially integrated by a holder 23 made of flexible black silicone rubber. In addition, the interval may be approximately 3 to 4 cm or more.

The light input unit 21 includes an optical fiber 24 and a prism 25, and is configured to input measurement light transmitted from a main unit 10 of the concentration measurement apparatus 1 substantially perpendicularly to a skin of the measurement target portion 51. The measurement light is, for example, pulsed laser light, and is sent from the main unit 10 (see FIG. 3).

The light detection unit 22 detects the measurement light propagated inside the measurement target portion 51, and generates an electrical detection signal according to an intensity of the measurement light. The light detection unit 22 is, for example, a one-dimensional photosensor (photodiode or the like), and includes N (N is an integer of 2 or more) arrayed photodetection elements 26 arranged in a distance direction from the light input unit 21.

The light detection unit 22 further includes a preamplifier unit 27 that integrates and amplifies a photocurrent output from the photodetection element 26. This makes it possible to detect a weak signal with high sensitivity to generate a detection signal, and transmit the signal to the main unit 10 (described later, see FIG. 3) via a cable 28. In addition, the light detection unit 22 may be a two-dimensional photosensor, or further, may be constituted by a charge-coupled device (CCD). The probe 20 may be fixed to a hairless portion such as a forehead by an adhesive tape or an elastic band.

Figure 3:
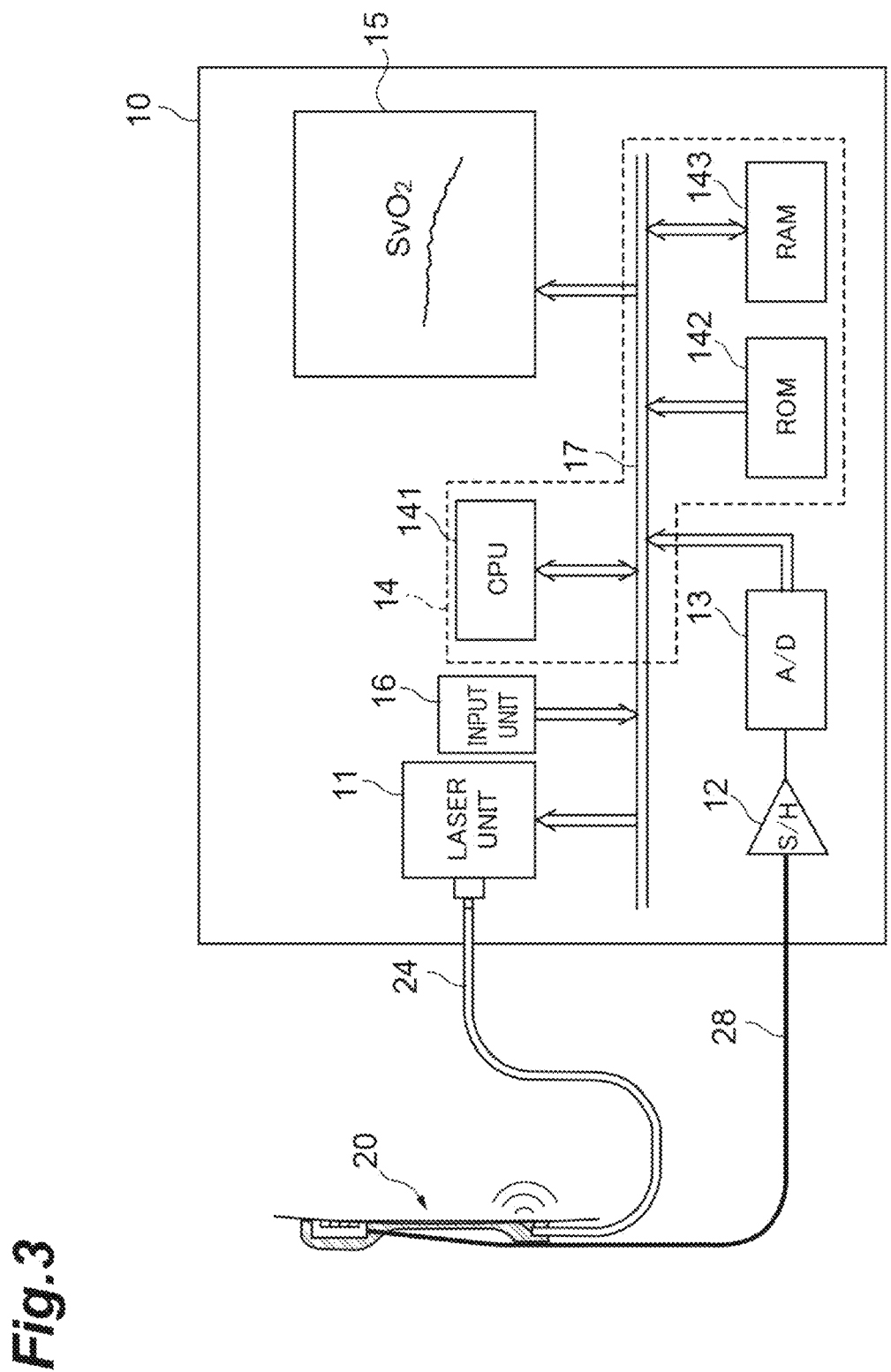
FIG. 3 is a block diagram illustrating a configuration example of the concentration measurement apparatus.

FIG. 3 is a block diagram illustrating a configuration example of the concentration measurement apparatus 1. The concentration measurement apparatus 1 illustrated in FIG. 3 includes the main unit 10 in addition to the probe 20 described above. The main unit 10 includes a light emitting unit 11, a sample-hold circuit 12, an A/D conversion circuit 13, a calculation unit 14, a display unit 15, an input unit 16, and a data bus 17.

The light emitting unit 11 includes a laser diode and a circuit for driving the laser diode. The light emitting unit 11 is electrically coupled to the data bus 17, and receives an instruction signal for instructing driving of the laser diode from the calculation unit 14, which is also electrically coupled to the data bus 17. The instruction signal includes information such as a light intensity and a wavelength (for example, one of the wavelengths $\lambda_1$, $\lambda_2$, $\lambda_3$) of laser light output from the laser diode.

The light emitting unit 11 drives the laser diode based on the instruction signal received from the calculation unit 14, and outputs the laser light to the probe 20 via the optical fiber 24. In addition, the light emitting element of the light emitting unit 11 does not have to be the laser diode, and may be any element that can sequentially output light of a plurality of wavelengths in a near-infrared region. Further, a light emitting diode such as an LED built in the probe 20 may be used as the light input unit 21.

The sample-hold circuit 12 and the A/D conversion circuit 13 receive the detection signal transmitted from the probe 20 via the cable 28, hold the signal, and convert the signal into a digital signal to output to the calculation unit 14. The sample-hold circuit 12 simultaneously holds the values of the N detection signals. The sample-hold circuit 12 is electrically coupled to the data bus 17, and receives a sample signal indicating the timing of holding the detection signal from the calculation unit 14 via the data bus 17. Upon receiving the sample signal, the sample-hold circuit 12 simultaneously holds the N detection signals input from the probe 20. The sample-hold circuit 12 is electrically coupled to the A/D conversion circuit 13, and outputs the held N detection signals to the A/D conversion circuit 13.

The A/D conversion circuit 13 converts the detection signal from an analog signal to a digital signal. The A/D conversion circuit 13 sequentially converts the N detection signals received from the sample-hold circuit 12 into the digital signals. The A/D conversion circuit 13 is electrically coupled to the data bus 17, and outputs the converted detection signal to the calculation unit 14 via the data bus 17.

The calculation unit 14 is a computer including a CPU 141, a ROM 142, and a RAM 143. In the calculation unit 14, the CPU 141 reads a program stored in the ROM 142, and the CPU 141 performs an operation according to the program, thereby realizing the functions described below. The calculation unit 14 may be configured by a microcomputer, a field programmable gate array (FPGA), or the like.

That is, the calculation unit 14 calculates required hemoglobin-related information in the measurement target portion 51 based on the detection signal received from the A/D conversion circuit 13. At this time, the calculation unit 14 performs the filter processing by a predetermined filter on the detection signal received from the A/D conversion circuit 13, the calculated $\Delta O_2Hb$ and/or $\Delta HHb$, or the numerical value appearing in the calculation process of $\Delta O_2Hb$ and/or $\Delta HHb$, thereby removing or reducing components in a band excluding a frequency band including a respiratory rate among frequency components included therein.

The calculation unit 14 sends the hemoglobin-related information thus calculated to the display unit 15 via the data bus 17. A method of calculating the hemoglobin-related information based on the detection signal and a method of filter processing will be described later. The display unit 15 is electrically coupled to the data bus 17 and displays the result sent from the calculation unit 14 via the data bus 17.

The input unit 16 inputs information on filter characteristics (center frequency, cutoff frequency, and the like) by an operation of the measurer. The input unit 16 may be constituted by, for example, a switch or a keyboard. The input unit 16 may directly input a numerical value related to the filter characteristics or may select one passband from a plurality of passbands. Further, the unit may be connected to a ventilator in a wired or wireless manner to receive a signal related to a set respiratory rate from the ventilator. The input unit 16 is electrically coupled to the data bus 17, and outputs information on the input filter characteristics (cutoff frequency, passband, set respiratory rate of ventilator, and the like) to the calculation unit 14 via the data bus 17.

Figure 4:
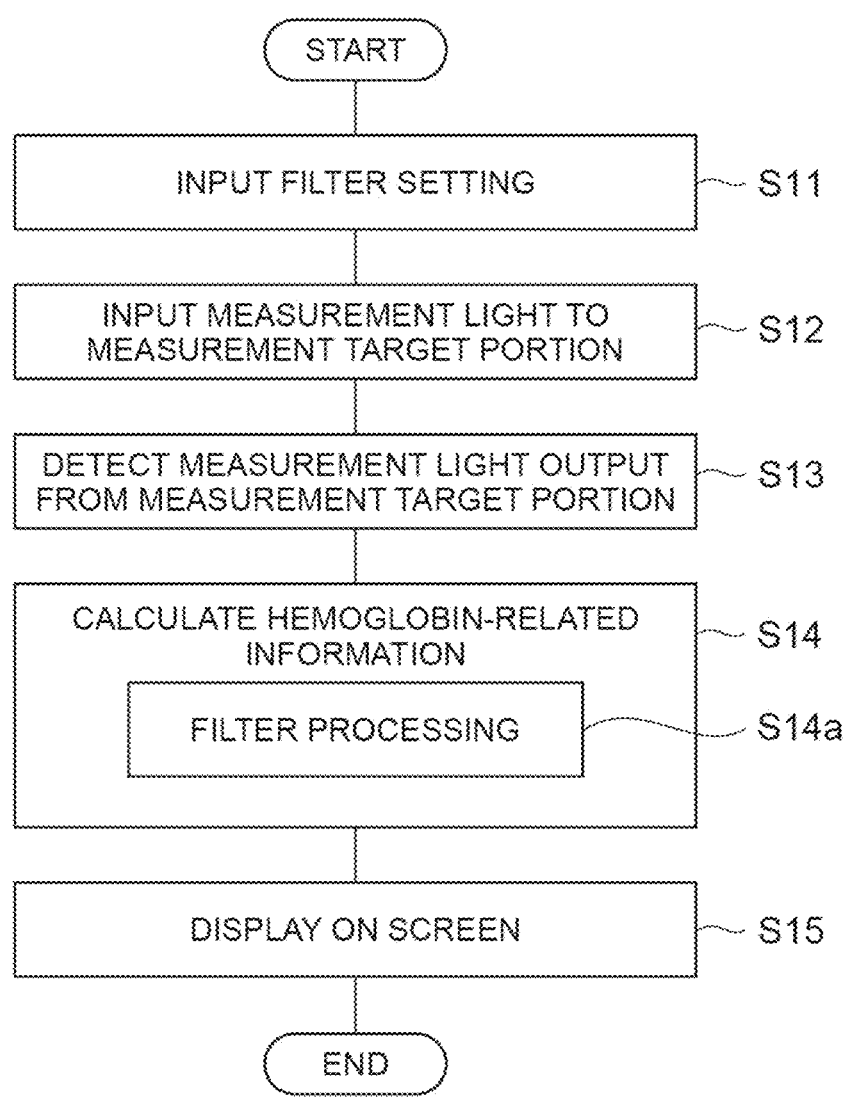
FIG. 4 is a flowchart illustrating a concentration measurement method according to an embodiment.

Next, operations of the concentration measurement apparatus 1 will be described. In addition, a concentration measurement method according to the present embodiment will be described. FIG. 4 is a flowchart illustrating the concentration measurement method according to the present embodiment.

First, the input unit 16 performs input of the filter characteristics (input of cutoff frequency and the like, selection of passband, or input of set respiratory rate of ventilator) (input step S11). In addition, the input step S11 is performed before a calculation step S14 described below, and for example, the step may be performed after a light input step S12 and a light detection step S13 described below. The input unit 16 outputs the obtained information to the calculation unit 14.

Subsequently, the light emitting unit 11 sequentially outputs the laser light of wavelengths $\lambda_1$ to $\lambda_3$ based on the instruction signal from the calculation unit 14. The laser light propagates through the optical fiber 24 to reach the light input position, and is input from the light input position into the measurement target portion 51 (light input step S12). The laser light input into the measurement target portion 51 propagates while being scattered in the measurement target portion 51 and absorbed by the measurement target component, and a part of the light reaches the light detection position.

The laser light reaching the light detection position is detected by the N photodetection elements 26 (light detection step S13). Each photodetection element 26 generates a photocurrent according to the detected laser light intensity. These photocurrents are converted into voltage signals (detection signals) by the preamplifier unit 27, and these voltage signals are sent to the sample-hold circuit 12 of the main unit 10 and held, and then converted into digital signals by the A/D conversion circuit 13.

Figure 5:
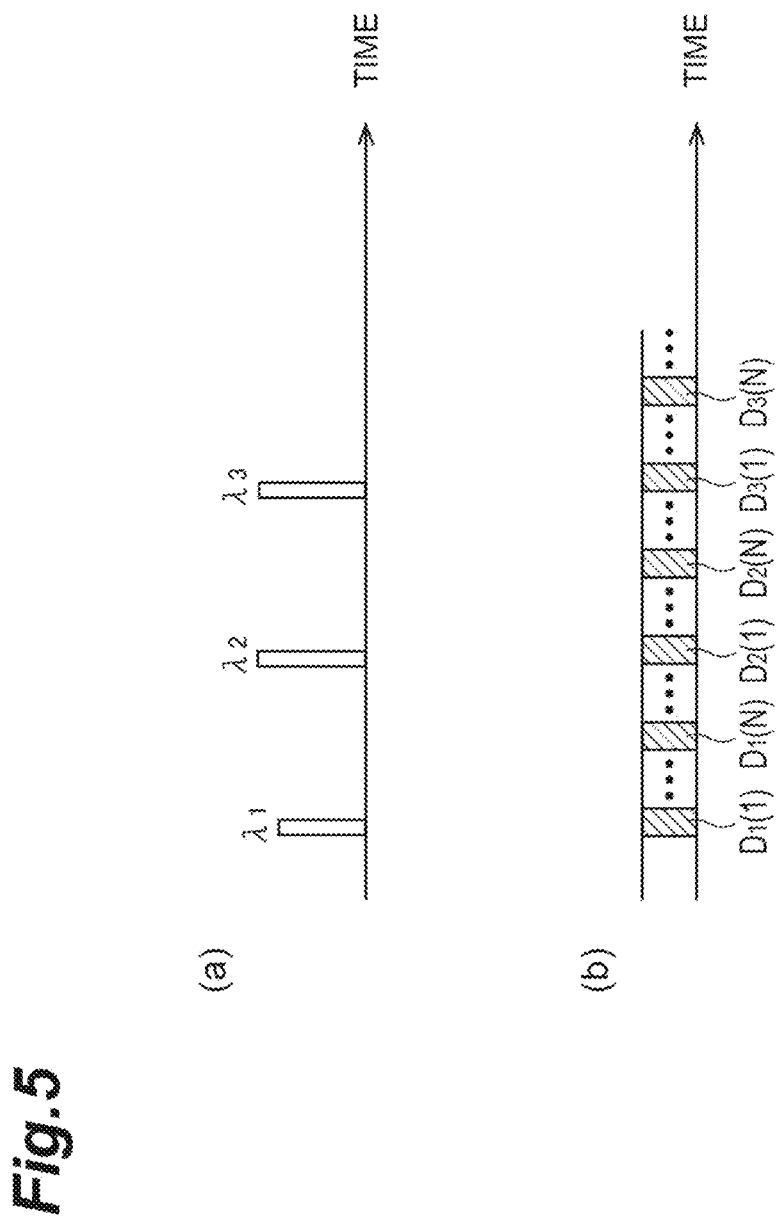
FIG. 5 includes (a) a diagram illustrating input timings of laser light having wavelengths $\lambda_1$ to $\lambda_3$, and (b) a diagram illustrating output timings of a digital signal from an A/D conversion circuit.

(a) in FIG. 5 is a diagram illustrating input timings of laser light of wavelengths $\lambda_1$ to $\lambda_3$, and (b) in FIG. 5 is a diagram illustrating output timings of digital signals from the A/D conversion circuit 13. As illustrated in FIG. 5, when the laser light of the wavelength $\lambda_1$ is input, the N digital signals $D_1(1)$ to $D_1(N)$ corresponding to the N photodetection elements 26 are sequentially obtained. Subsequently, when the laser light of the wavelength $\lambda_2$ is input, the N digital signals $D_2(1)$ to $D_2(N)$ corresponding to the N photodetection elements 26 are sequentially obtained. In this manner, the (3×N) digital signals $D_1(1)$ to $D_3(N)$ are output from the A/D conversion circuit 13.

Subsequently, the calculation unit 14 calculates one or both of $\Delta O_2Hb$ and $\Delta HHb$ based on the digital signals $D_1(1)$ to $D_3(N)$. In addition, the calculation unit 14 calculates other hemoglobin-related information such as $\Delta cHb$ and $StO_2$ based on the obtained $\Delta O_2Hb$ and $\Delta HHb$ (calculation step S14). $StO_2$ is a hemoglobin oxygen saturation including both arteries and veins.

At this time, the calculation unit 14 performs the filter processing on any of the detection signal received from the A/D conversion circuit 13, the calculated hemoglobin-related information, or the numerical value appearing in the calculation process of the hemoglobin-related information (filter processing step S14a). In this filter processing, based on the cutoff frequency or the passband input or selected in the input step S11, or the passband determined from the set respiratory rate of the ventilator, among the frequency components included in the hemoglobin-related information, the components of the band excluding the frequency band including the respiratory rate are removed or reduced. Thus, the component derived from respiration are extracted from the hemoglobin-related information.

The calculated hemoglobin-related information is displayed on the display unit 15 (step S15). In the concentration measurement apparatus 1 and the concentration measurement method according to the present embodiment, the steps S12 to S15 described above are repeated.

The calculation content of the calculation unit 14 in the calculation step S14 will be described in detail. In the following description, as an example, the hemoglobin-related information is first calculated, and then the filter processing is performed on the hemoglobin-related information. The timing of the filter processing is not limited thereto, and for example, the processing may be performed on the digital signals $D_1(1)$ to $D_3(N)$ before the calculation, or may be performed on any of various numerical values appearing in the process of calculating the hemoglobin-related information from the digital signals $D_1(1)$ to $D_3(N)$.

For a certain light detection position, assuming that the values of the detection signals according to the laser light wavelengths $\lambda_1$ to $\lambda_3$ at a time $T_0$ are $D\lambda_1(T_0)$ to $D\lambda_3(T_0)$, and the values at a time $T_1$ are $D\lambda_1(T_1)$ to $D\lambda_3(T_1)$, the change amount of the detected light intensity from the time $T_0$ to the time $T_1$ is expressed as the following Formulas (1) to (3).

[Formula 1]
$$\Delta OD_1(T_1) = \log\left(\frac{D_{\lambda_1}(T_1)}{D_{\lambda_1}(T_0)}\right) \quad (1)$$

[Formula 2]
$$\Delta OD_2(T_1) = \log\left(\frac{D_{\lambda_2}(T_1)}{D_{\lambda_2}(T_0)}\right) \quad (2)$$

[Formula 3]
$$\Delta OD_3(T_1) = \log\left(\frac{D_{\lambda_3}(T_1)}{D_{\lambda_3}(T_0)}\right) \quad (3)$$

In Formulas (1) to (3), $\Delta OD_1(T_1)$ is the temporal relative change amount of the detected light intensity at wavelength $\lambda_1$, $\Delta OD_2(T_1)$ is the temporal relative change amount of the detected light intensity at wavelength $\lambda_2$, and $\Delta OD_3(T_1)$ is the temporal relative change amount of the detected light intensity at wavelength $\lambda_3$.

Further, when the temporal relative change amounts of the concentrations of oxygenated hemoglobin ($O_2Hb$) and deoxygenated hemoglobin (HHb) from the time $T_0$ to the time $T_1$ are $\Delta O_2Hb(T_1)$ and $\Delta HHb(T_1)$, these can be obtained by the following Formula (4).

[Formula 4]
$$\begin{pmatrix} \Delta O_2Hb(T_1) \\ \Delta HHb(T_1) \end{pmatrix} = \begin{pmatrix} a_{11} & a_{12} & a_{13} \\ a_{21} & a_{22} & a_{23} \end{pmatrix} \begin{pmatrix} \Delta OD_1(T_1) \\ \Delta OD_2(T_1) \\ \Delta OD_3(T_1) \end{pmatrix} \quad (4)$$

In Formula (4), coefficients $a_{11}$ to $a_{23}$ are constants obtained from extinction coefficients of $O_2Hb$ and HHb for light of wavelengths $\lambda_1$, $\lambda_2$, and $\lambda_3$. The temporal relative change amount $\Delta cHb(T_1)$ of the total hemoglobin concentration in the measurement target portion 51 can be obtained by the following Formula (5).

[Formula 5]
$$\Delta cHb(T_1) = \Delta O_2Hb(T_1) + \Delta HHb(T_1) \quad (5)$$

Further, the calculation unit 14 performs, for example, any one of the following filter processing on at least one of $\Delta O_2Hb$, $\Delta HHb$, and $\Delta cHb$ calculated as described above.

(1) Filter Processing by a Digital Filter

A data string related to $\Delta O_2Hb$, $\Delta HHb$, $\Delta cHb$ obtained in a predetermined cycle is represented by $X(n)$. Here, n is an integer. For example, for the data string $X(n)$, the following filter coefficients $A(n)$ are multiplied to the data with n=0 as a time center, and the results are added to realize a non-recursive linear phase digital filter. The following values are an example of a filter for extracting a component of 10 bpm (beat per minute) being a ventilation frequency of a standard ventilator.

$A(0) = 0.213$ $A(1) = A(-1) = 0.164$ $A(2) = A(-2) = 0.064$ $A(3) = A(-3) = -0.039$ $A(4) = A(-4) = -0.098$ $A(5) = A(-5) = -0.096$ $A(6) = A(-6) = -0.064$ $A(7) = A(-7) = -0.029$ $A(8) = A(-8) = -0.009$

More specifically, a delay operator for the data string $X(n)$ is represented by the following Formula (6). Here, f is a time frequency (unit: 1/sec). Further, $\omega$ is an angular frequency, and $\omega = 2\pi f$. Further, T is a cycle at which the data string $X(n)$ is obtained, and is set to a cycle of, for example, 0.5 seconds for measuring a variation waveform up to about 15 times per minute (0.25 Hz).

[Formula 6]

$$e^{j\omega nT} = \cos(\omega nT) + j\sin(\omega nT)$$

$$e^{-j\omega nT} = \cos(\omega nT) - j\sin(\omega nT) \quad (6)$$

In this case, the digital filter characteristics when the above-described filter coefficients $A(n)$ are used are described by the following Formula (7).

[Formula 7]

$$R(\omega) = \quad (7)$$

$$A(0) + \sum_{n=1}^{8} A(n) \cdot (e^{-jn\omega t} + e^{+jn\omega t}) = A(0) + \sum_{n=1}^{8} 2 \cdot A(n) \cdot \cos(n\omega t)$$

$$R(\omega) = 0.213 + 0.164(e^{-2j\omega t} + e^{+2j\omega t}) + 0.064(e^{-4j\omega t} + e^{+4j\omega t}) -$$
$$0.039(e^{-6j\omega t} + e^{+6j\omega t}) - 0.098(e^{-8j\omega t} + e^{+8j\omega t}) -$$
$$0.096(e^{-10j\omega t} + e^{+10j\omega t}) - 0.064(e^{-12j\omega t} + e^{+12j\omega t}) -$$
$$0.029(e^{-14j\omega t} + e^{+14j\omega t}) - 0.009(e^{-16j\omega t} + e^{+16j\omega t})$$
$$= 0.213 + 0.328 \cdot \cos(2\omega t) + 0.128 \cdot \cos(4\omega t) -$$
$$0.078 \cdot \cos(6\omega t) - 0.196 \cdot \cos(8\omega t) - 0.192 \cdot \cos(10\omega t) -$$
$$0.128 \cdot \cos(12\omega t) - 0.058 \cdot \cos(14\omega t) - 0.018 \cdot \cos(16\omega t)$$

In this manner, the digital filter is represented by a product-sum operation of the data string $X(n)$ and the corresponding coefficients.

Further, when the time frequency f in Formula (7) is converted into a time frequency F per minute (unit: 1/min), the following Formula (8) is obtained.

[Formula 8]

$$R(F) = A(0) + 2 \cdot \sum_{n=1}^{8} A(n) \cdot \cos\left(\frac{n\pi}{60}F\right) \quad (8)$$

$$R(F) = 0.213 + 0.328 \cdot \cos\left(\frac{2\pi}{60}F\right) + 0.128 \cdot \cos\left(\frac{4\pi}{60}F\right) -$$
$$0.078 \cdot \cos\left(\frac{6\pi}{60}F\right) - 0.196 \cdot \cos\left(\frac{8\pi}{60}F\right) - 0.192 \cdot \cos\left(\frac{10\pi}{60}F\right) -$$
$$0.128 \cdot \cos\left(\frac{12\pi}{60}F\right) - 0.058 \cdot \cos\left(\frac{14\pi}{60}F\right) - 0.018 \cdot \cos\left(\frac{16\pi}{60}F\right)$$

Figure 6:
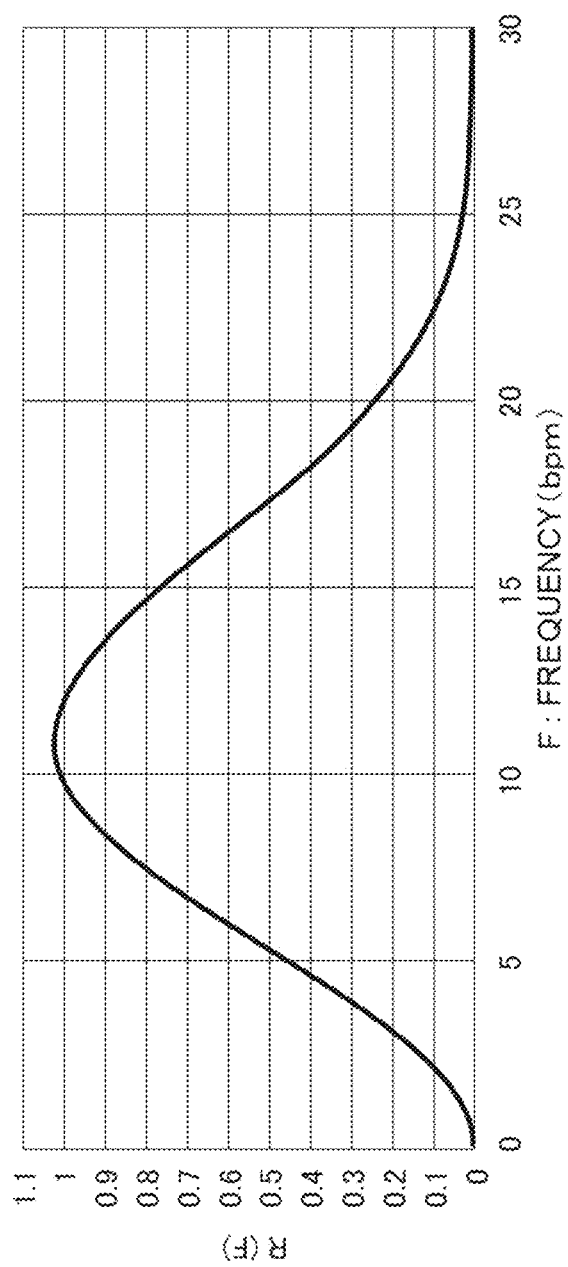
FIG. 6 is a diagram of a graph of R (F) illustrating filter characteristics of a digital filter.

FIG. 6 is a graph of R(F) showing the filter characteristics of the digital filter. In FIG. 6, the horizontal axis represents the respiratory rate per minute (unit: bpm), and the vertical axis represents the value of R(F). When the cycle T is 0.5 seconds, this filter is a band-pass filter having a pass peak near 10 bpm (0.17 Hz). With such a digital filter, the time variation component derived from respiration can be suitably extracted.

(2) Filter Processing by a Smoothing Operation (Least Square Error Curve Fitting)

With n=0 as the time center in the above-described data string X(n), a least square error curve fitting using a high-order function (for example, a fourth-order function) is performed on the data string X(n) obtained in a predetermined time (for example, 30 seconds, 5 respirations) before and after the time center. The constant term of the obtained high-order function is then regarded as a smoothed component (frequency component less than the cutoff frequency) at n=0. That is, by subtracting the smoothed frequency component from the original data X(0), the frequency component less than the cutoff frequency of the low frequency side can be removed from the frequency components included in the temporal relative change amount, and the time variation component derived from respiration can be separated and extracted.

(3) Filter Processing of Uniformizing the Maximum Portions or the Minimum Portions of Variation (a) in FIG. 7 and (b) in FIG. 7 are diagrams for explaining the concept of the present filter processing. In this filter processing, for example, the maximum values in $\Delta O_2Hb$, $\Delta HHb$, or $\Delta cHb$ are obtained, and as shown in (a) in FIG. 7, the maximum values P1 in the time variation graph G11 are regarded as a constant value, thereby removing frequency components less than the cutoff frequency of the low frequency side included in $\Delta O_2Hb$, $\Delta HHb$, or $\Delta cHb$. Alternatively, for example, the minimum values in $\Delta O_2Hb$, $\Delta HHb$, or $\Delta cHb$ are obtained, and as shown in (b) in FIG. 7, the minimum values P2 in the time variation graph G12 are regarded as a constant value, thereby removing frequency components less than the cutoff frequency of the low frequency side included in $\Delta O_2Hb$, $\Delta HHb$, or $\Delta cHb$. As described above, by bringing the maximum values P1 and/or the minimum values P2 close to the constant value, the time variation component derived from respiration can be suitably extracted.

The filter characteristics set in the filter processing step S14a will be described in detail. The following Table 1 is a table showing average respiratory rates of healthy persons at rest. Further, the ventilation rate of the ventilator may be set to a value outside the following ranges.

TABLE 1

| Age | Rate |
|---|---|
| 6 weeks (newborn) | 30-60/minute |
| 6 months | 25-40/minute |
| 3 years | 20-30/minute |
| 6 years | 18-25/minute |
| 10 years | 17-23/minute |
| adult | 12-18/minute |
| elderly person of 65 years old or older | 12-28/minute |
| elderly person of 80 years old or older | 10-30/minute |

Figure 8:
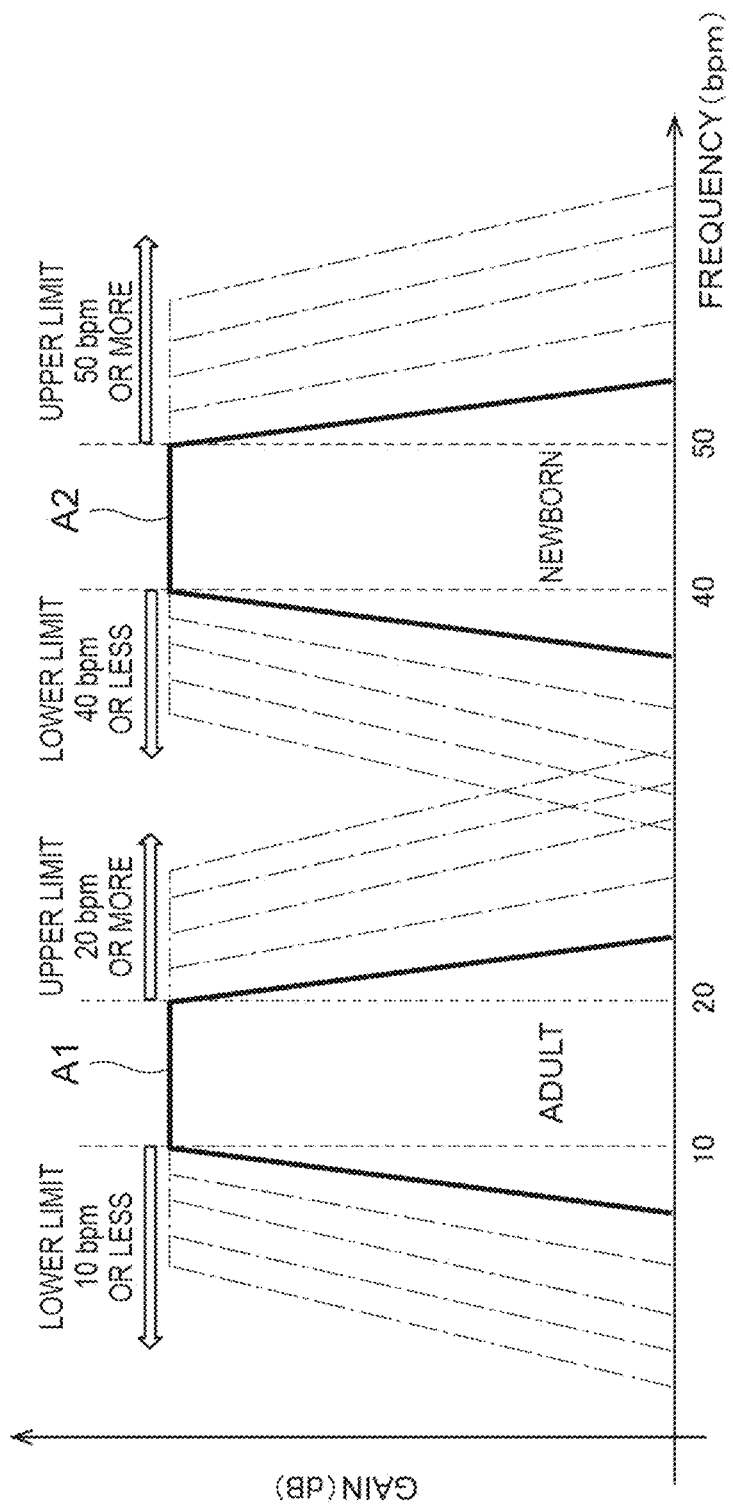
FIG. 8 is a graph conceptually illustrating a passband of a filter.

In the calculation unit 14 and the filter processing step S14a of the present embodiment, a passband of the filter is set based on the above respiratory rate at rest. FIG. 8 is a graph conceptually illustrating the passband of the filter, the horizontal axis represents frequency (unit: bpm), and the vertical axis represents gain (unit: dB). As shown in the waveform A1 of FIG. 8, for example, when the subject is an adult, ideally, preferably, the cutoff frequency of the low frequency side is set to 10 bpm or less, and the cutoff frequency of the high frequency side is set to 20 bpm or more. Further, as shown in the waveform A2 of FIG. 8, for example, when the subject is a newborn, ideally, preferably, the cutoff frequency of the low frequency side is set to 40 bpm or less, and the cutoff frequency of the high frequency side is set to 50 bpm or more.

Further, from the viewpoint of measurement accuracy and the like, it may not be necessary to finely define the passband of the filter for each age group described in above Table 1. In such a case, for example, the cutoff frequency of the low frequency side may be set in a range of 10 bpm (0.17 Hz) or more and 30 bpm (0.5 Hz) or less, and the cutoff frequency of the high frequency side may be set in a range of 30 bpm (0.5 Hz) or more and 60 bpm (1.0 Hz) or less.

As is clear from Table 1, a respiratory rate of persons decreases with age, and the respiratory rate of newborns is 30 to 60 bpm, whereas the respiratory rate of elderly persons of 80 years old or older is 10 to 30 bpm. Therefore, by setting the cutoff frequencies of the low frequency side and the high frequency side in this manner, subjects of various ages from newborns to elderly persons can be handled.

Further, in the input unit 16 and the input step S11, when one passband can be selected from a plurality of passbands set in advance, the plurality of passbands may include a first passband included in a range of 10 bpm (0.17 Hz) or more and 30 bpm (0.5 Hz) or less corresponding to children, adults, or elderly persons, and a second passband included in a range of 30 bpm (0.5 Hz) or more and 60 bpm (1.0 Hz) or less corresponding to newborns and babies. Further, the plurality of passbands may include a first passband including at least a range of 10 bpm or more and 20 bpm or less and a second passband including at least a range of 40 bpm or more and 50 bpm or less.

When one passband can be selected from the plurality of passbands, an appropriate passband can be easily set according to the respiratory rate of the subject. Further, when the above first and second passbands are included in the plurality of passbands, subjects of various ages from newborns to elderly persons can be handled. In addition, the plurality of passbands to be selected are stored in advance in the ROM 142 or the like.

Further, when the ventilator is attached to the subject, the passband of the filter may be set such that the set respiratory rate of the ventilator is included in the passband of the filter. In this case, the filter characteristics may be set such that the set respiratory rate of the ventilator becomes a center frequency (peak frequency) of the passband, or the passband may be set with predetermined frequency margins on the high frequency side and the low frequency side for the set respiratory rate.

In general, the magnitude of pressurization in the ventilator is larger than the magnitude of depressurization (depth of respiration) in the spontaneous respiration, and thus, the subject using the ventilator has a large periodic variation of the hemoglobin-related information derived from respiration. Further, unlike the spontaneous respiration, the ventilation cycle of the ventilator hardly changes and is maintained constant with high accuracy. Therefore, it is easy to accurately extract only the periodic variation component derived from respiration from the hemoglobin-related information, and thus, the hemoglobin-related information of veins can be more accurately and easily obtained.

In particular, when the signal related to the set respiratory rate is provided from the ventilator in the input unit 16 and the input step S11, the passband may be manually input or automatically determined in the calculation unit 14 and the filter processing step S14a according to the set respiratory rate (to be included in the passband of the filter). Accordingly, the set respiratory rate of the ventilator can be easily included in the passband of the filter.

Effects of the concentration measurement apparatus 1 and the concentration measurement method according to the present embodiment having the above configuration will be described.

In a certain measurement opportunity, the present inventors have observed measurement results of the hemoglobin-related information in detail, and have found a clearly periodic variation waveform by chance. This variation was considered to be a beat component between the heart rate and the measurement frequency (2 Hz), but the variation cycle was 6 seconds (0.166 Hz) and the heart rate of the subject was around 70 beats per minute (1.16 Hz), and thus, the possibility thereof was low, and since the cycle was extremely stable, it was difficult to consider the variation to be caused by a physiological phenomenon. Thereafter, it was confirmed that the cycle of this variation accurately coincided with the ventilation cycle of the ventilator.

At the time of the measurement, the probe was fixed to the forehead of the subject. Therefore, it is considered that this variation is not derived from mechanical movement of a throat, lung, chest, or the like, but is derived from expansion and contraction of brain blood vessels due to ventilation pressure. Further, the hemoglobin-related information in blood mainly in capillaries is measured by a concentration measurement apparatus using light. Therefore, it can be said that this variation is derived from expansion and contraction of capillaries in the brain tissue.

Figure 9:
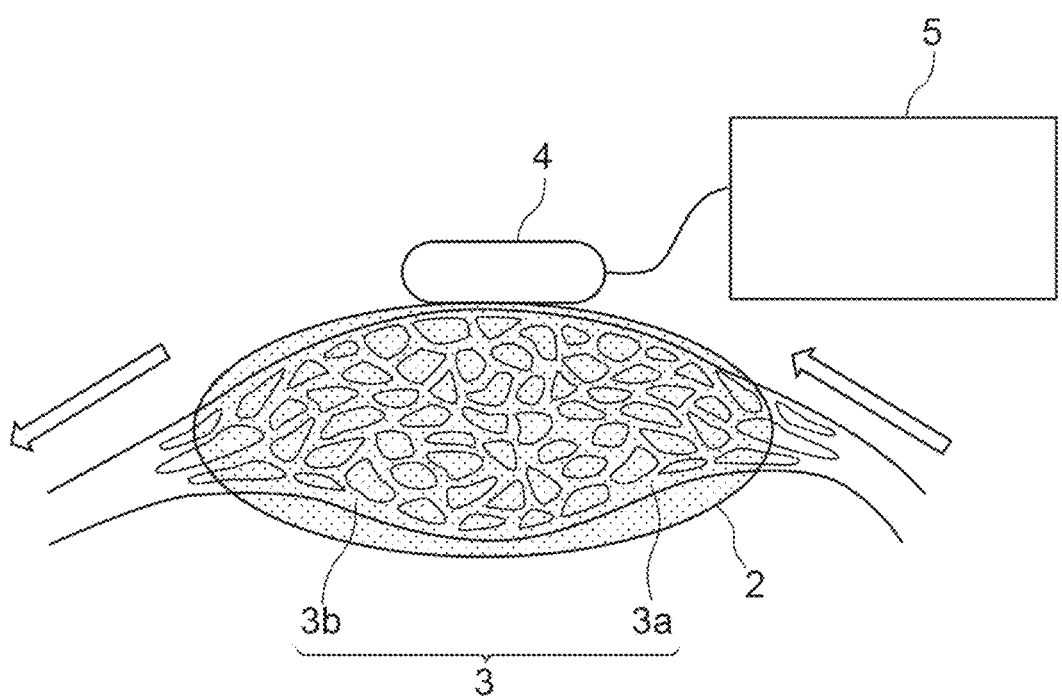
FIG. 9 is a diagram schematically illustrating a blood vessel of a certain body tissue and a concentration measurement apparatus including a probe.
Figure 10:
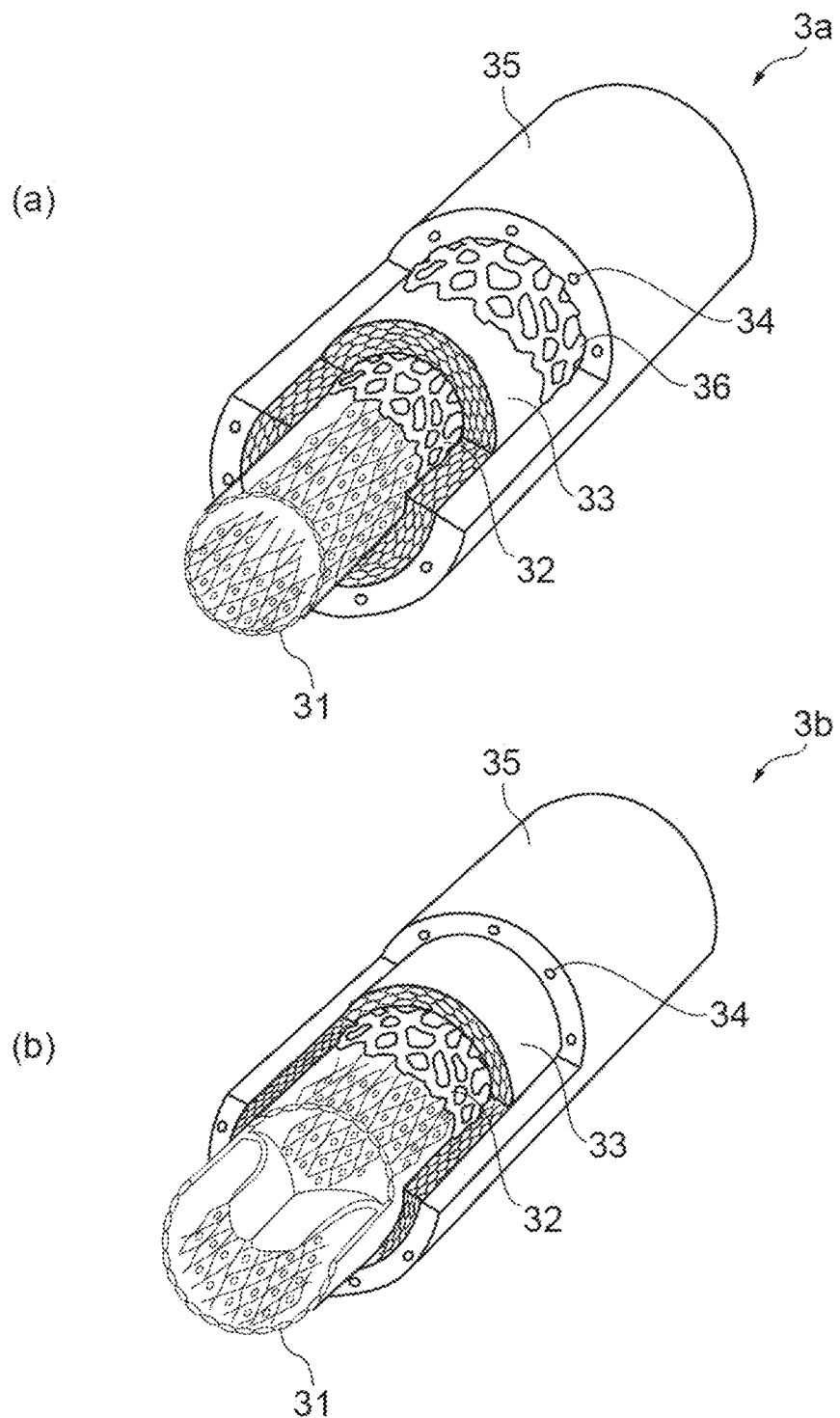
FIG. 10 includes (a) a perspective cross-sectional view illustrating a cross-sectional structure of a capillary of an arterial system, and (b) a perspective cross-sectional view illustrating a cross-sectional structure of a capillary of a venous system.

FIG. 9 is a diagram schematically illustrating a blood vessel 3 of a certain body tissue 2 and a concentration measurement apparatus 5 including a probe 4. In the body tissue 2, arterial system capillaries 3a and venous system capillaries 3b are mixed. In general, hemoglobin-related information measured by the concentration measurement apparatus 5 includes information on both the arterial system and venous system capillaries 3a and 3b. (a) in FIG. 10 is a perspective cross-sectional view illustrating a cross-sectional structure of the capillary 3a of the arterial system, and (b) in FIG. 10 is a perspective cross-sectional view illustrating a cross-sectional structure of the capillary 3b of the venous system.

Each of the capillaries 3a and 3b includes an intima (endothelium) 31, an elastic membrane 32 covering the intima 31, a tunica media (smooth muscle) 33 covering the elastic membrane 32, a nutrient vessel 34 covering the tunica media 33, and an adventitia 35 covering the nutrient vessel 34. The capillary 3a of the arterial system further includes another elastic membrane 36 between the tunica media 33 and the nutrient vessel 34. As illustrated in (a) in FIG. 10, the capillary 3a of the arterial system has a strong structure in which the blood vessel wall (tunica media 33 and adventitia 35) is thick for maintaining a blood transmission function by withstanding a large blood pressure variation due to heartbeat. On the other hand, in the capillary 3b of the venous system, since the blood pressure is low and there is almost no variation, as illustrated in (b) in FIG. 10, the blood vessel wall (tunica media 33 and adventitia 35) of the capillary 3b of the venous system is extremely thin and has a flexible structure as compared with the capillary 3a of the arterial system.

When a person breathes (or periodically ventilates with a ventilator), a change in intrathoracic pressure caused by it spreads to other portions in a body, causing a change in body cavity pressure at each portion. The above pressure is exerted on the capillaries in each portion, and the influence of the pressure is larger in the capillary 3b of the venous system than in the capillary 3a of the arterial system, because the blood vessel wall of the capillary 3b of the venous system is thin and flexible while the blood vessel wall of the capillary 3a of the arterial system is thick and strong as described above. Therefore, it is considered that the variation of the intrathoracic pressure due to respiration induces expansion and contraction almost only in the capillary 3b of the venous system, and specifically varies the hemoglobin-related information of the vein blood. The periodic variation of the hemoglobin-related information described above is caused by repeated expansion and contraction of the blood vessel wall of the capillary 3b of the venous system due to the influence of the above pressure.

Further, variation caused by heartbeat also occurs in the hemoglobin-related information measured in the concentration measurement apparatus 5. However, this variation occurs in the capillary 3a of the arterial system, and the variation cycle coincides with the heartbeat cycle, and is, for example, about 90 times per minute. On the other hand, the cycle of variation due to respiration is, for example, about 10 to 60 times per minute, which is clearly different from the cycle of variation due to heartbeat. From this, it can be said that the hemoglobin-related information of the capillary 3b of the venous system can be selectively obtained by extracting only the periodic variation component derived from respiration from the hemoglobin-related information.

In view of this, in the present embodiment, when hemoglobin-related information is obtained based on the detection result of the measurement light propagated inside the measurement target portion 51, the calculation unit 14 (in the calculation step S14) selectively obtains the hemoglobin-related information in the vein of the measurement target portion 51 by performing the filter processing for extracting a component derived from respiration among frequency components included in the detection signal, the hemoglobin-related information, or the numerical value appearing in the calculation process of the hemoglobin-related information. Thus, the hemoglobin-related information of veins can be obtained non-invasively using light.

In addition, the hemoglobin oxygen saturation ($StO_2$ or TOI) measured in the conventional concentration measurement apparatus is an average value of the entire tissue including both arteries and veins, and is represented by the following Formula (9). Here, $SaO_2$ is a hemoglobin oxygen saturation of arteries, R is a volume ratio of arteries in entire capillaries, and (1−R) is a volume ratio of veins.

[Formula 9]

$$StO_2 = R \cdot SaO_2 + (1-R) \cdot SvO_2 \qquad (9)$$

The parameter that directly reflects tissue metabolism is $SvO_2$, but R is unknown and varies depending on the subject and the case. Therefore, in the conventional method, the hemoglobin oxygen saturation ($SvO_2$) of veins cannot be obtained from $StO_2$.

On the other hand, in the present embodiment, $SvO_2$ can be calculated by the following Formula (10) based on $\Delta vO_2Hb$ which is $\Delta O_2Hb$ of veins and $\Delta vHHb$ which is $\Delta HHb$ of veins. Further, since this calculation is based on the ratio of the change amounts of $O_2Hb$ and $HHb$, it is possible to stably measure $SvO_2$ with less influence of the shape of the measurement target portion 51, the mounting state of the probe 20, and the like.

[Formula 10]

$$SvO_2 = \frac{\Delta vO_2Hb}{\Delta vO_2Hb + \Delta vHHb} \qquad (10)$$

Figure 11:
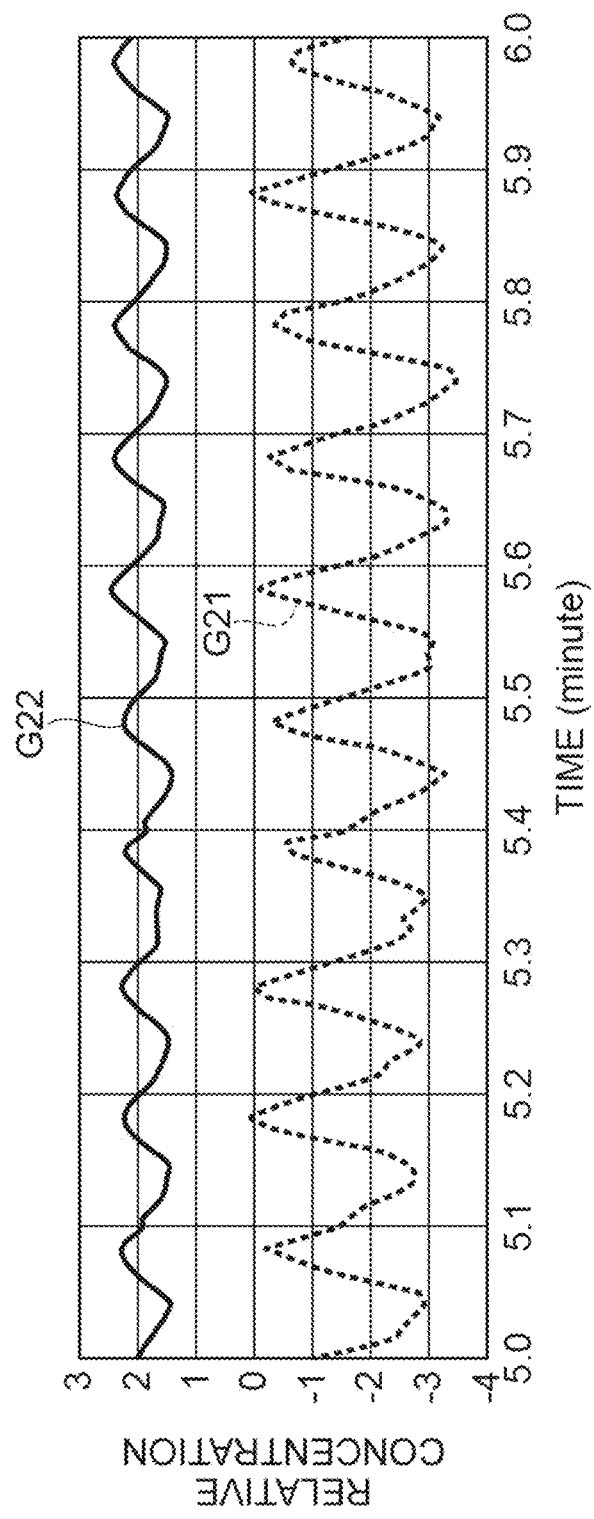
FIG. 11 is a partially enlarged graph of time changes of $\Delta O_2Hb$ and $\Delta HHb$ before the filter processing, actually measured in a subject during cardiac surgery with a ventilator.
Figure 12:
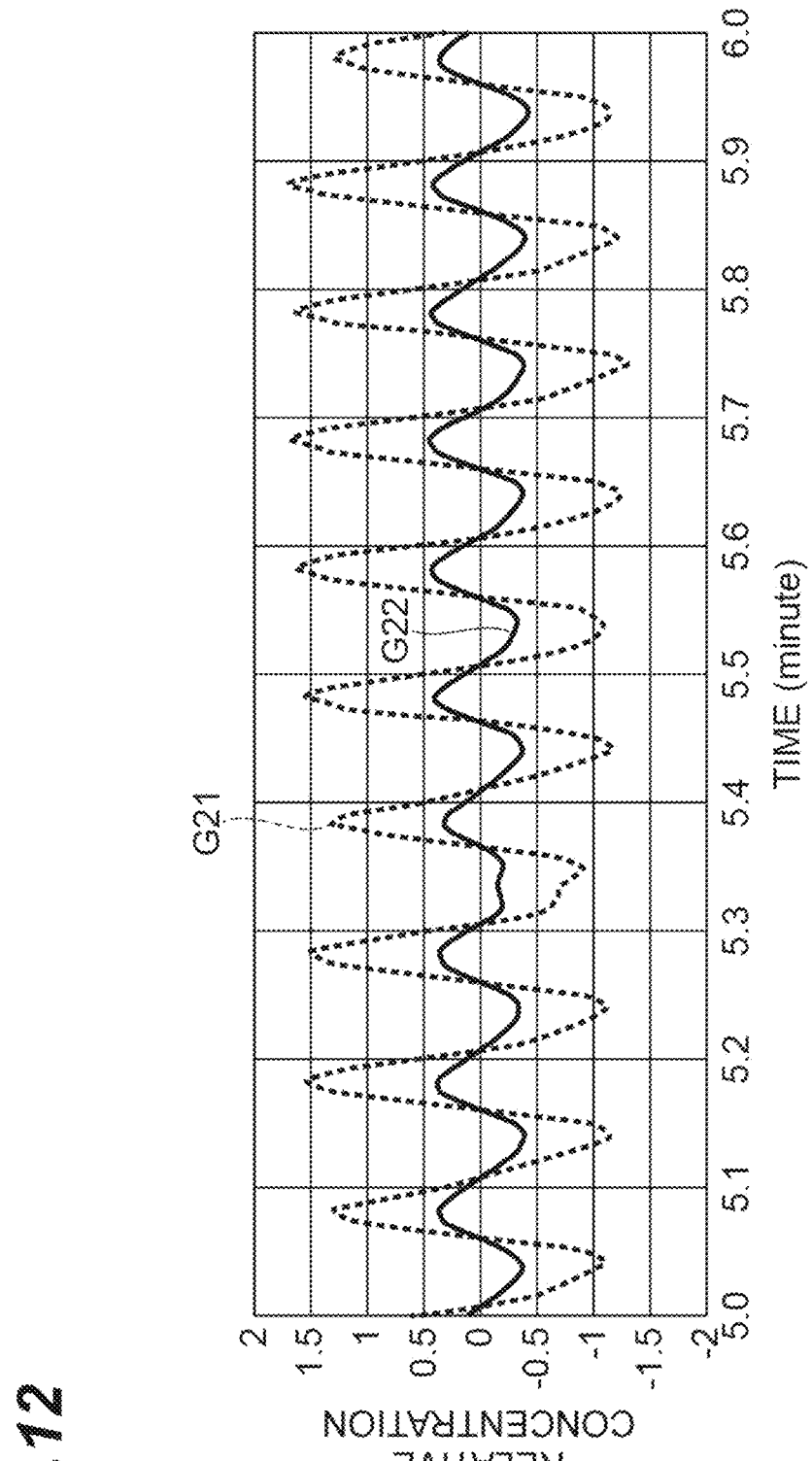
FIG. 12 is a partially enlarged graph of time changes of $\Delta O_2Hb$ and $\Delta HHb$ after the filter processing.

FIG. 11 is a partially enlarged graph of time changes of $\Delta O_2Hb$ and $\Delta HHb$ before the filter processing, actually measured in a subject during cardiac surgery with a ventilator. Further, FIG. 12 is a partially enlarged graph of time changes of $\Delta O_2Hb$ and $\Delta HHb$ after the filter processing (that is, $\Delta vO_2Hb$ and $\Delta vHHb$). In FIG. 11 and FIG. 12, a graph G21 indicates $\Delta O_2Hb$, and a graph G22 indicates $\Delta HHb$. The vertical axis represents change amount (arbitrary unit), and the horizontal axis represents time (unit: minute). Referring to the graphs G21 and G22, periodic variations of about 10 times per minute derived from respiration are observed.

Figure 13:
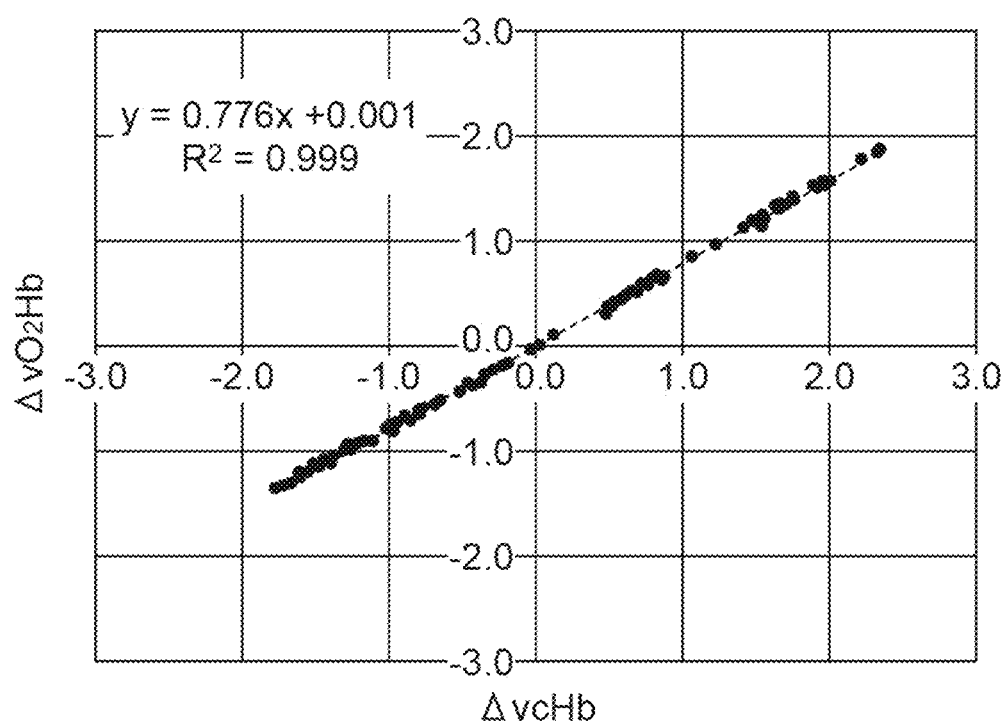
FIG. 13 is a scatter diagram illustrating a correlation between $\Delta vO_2Hb$ and a total hemoglobin concentration ($\Delta vcHb$) of a vein which is a sum of an oxygenated hemoglobin concentration ($\Delta vO_2Hb$) of the vein and a deoxygenated hemoglobin concentration ($\Delta vHHb$) of the vein being periodic variation components extracted from graphs G21 and G22.

FIG. 13 is a scatter diagram illustrating a correlation between $\Delta vO_2Hb$ and a variation component ($\Delta vcHb$) of a total hemoglobin concentration of veins, which is a sum of $\Delta vO_2Hb$ and $\Delta vHHb$ being periodic variation components extracted from the graphs G21 and G22. According to this figure, $\Delta vcHb$ and $\Delta vO_2Hb$ are proportional to each other with a high correlation (square value of correlation coefficient R is $R^2=0.999$), and a proportionality coefficient (0.776, that is 77.6% in this example) corresponds to the hemoglobin oxygen saturation ($SvO_2$) of veins.

Figure 14:
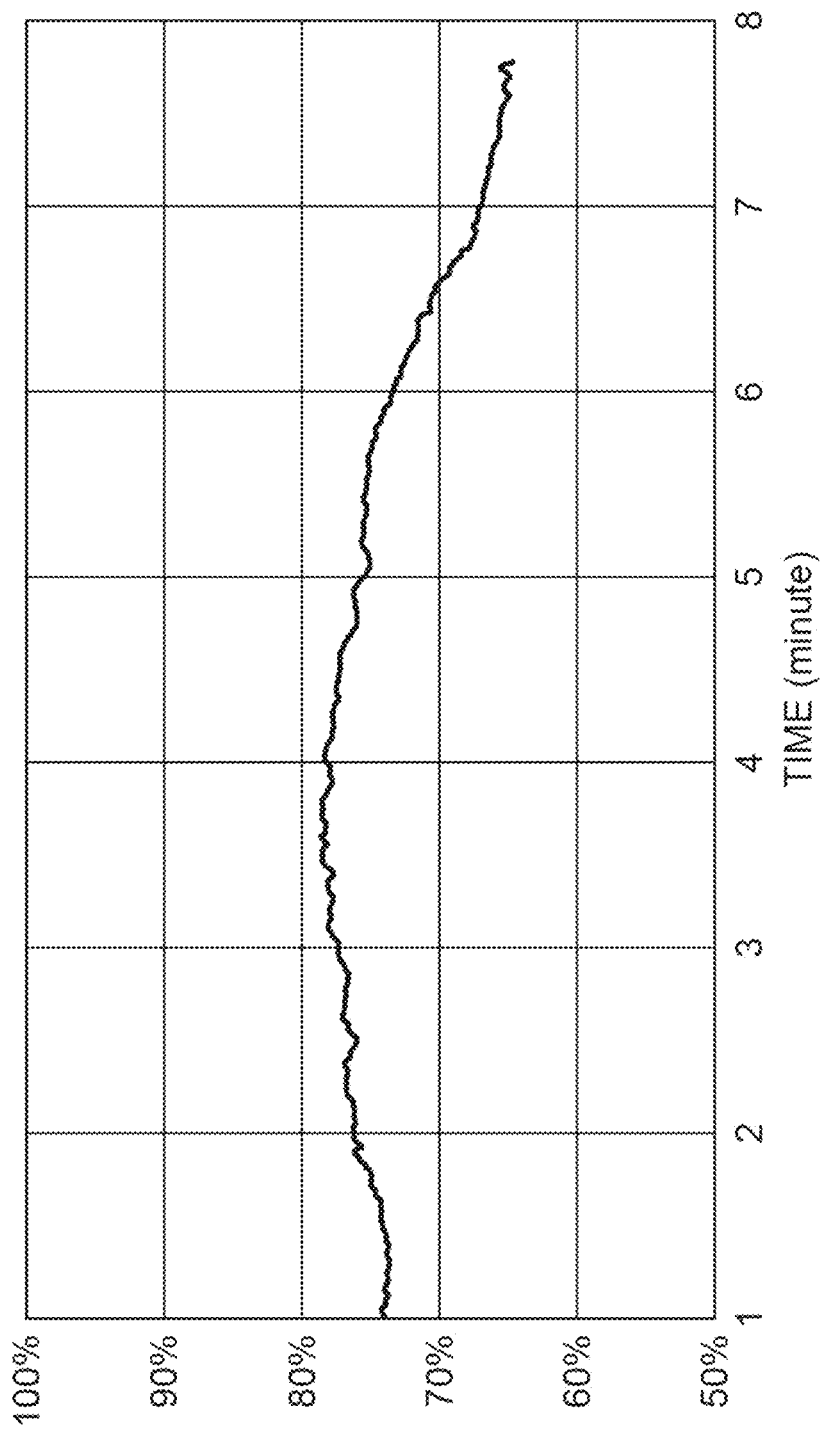
FIG. 14 is a graph of a time change of $SvO_2$.

FIG. 14 is a graph of a time change of $SvO_2$. The vertical axis represents $SvO_2$ (unit: %), and the horizontal axis represents time (unit: minute). As described above, the hemoglobin-related information such as $SvO_2$ can be suitably calculated by performing the filter processing for extracting a component derived from respiration. In particular, when the measurement target portion 51 is a brain, $SvO_2$ is an amount reflecting oxygen consumption in the brain, and is a clinically important parameter indicating brain metabolism.

Further, as described above, in the present embodiment, variation derived from respiration is extracted from the hemoglobin-related information, and "respiration" may be spontaneous respiration or ventilation by a ventilator. In either case, the above-described effects can be expected. In addition, the ventilation by the ventilator is in general deeper than the spontaneous respiration and the cycle is accurately constant, and thus, the extraction accuracy of the variation component tends to be high. Therefore, when the ventilator is used, the accuracy of measuring the hemoglobin-related information of veins is higher than when it is not used. The ventilator is mainly used for a patient during surgery or a patient in an intensive care unit (ICU), and accordingly, the concentration measurement apparatus 1 and the concentration measurement method according to the present embodiment are more effective when these patients are subjects.

Further, the hemoglobin oxygen saturation ($SaO_2$) of arteries can be easily obtained from the ratio between $\Delta O_2Hb$ and $\Delta HHb$ that varies in synchronization with the heartbeat. By calculating the difference ($SaO_2-SvO_2$) between this $SaO_2$ and $SvO_2$ measured by the present embodiment, a more direct evaluation of oxygen consumption in the measurement target portion is possible. Therefore, for example, when the measurement target portion is a brain, both $SaO_2$ and $SvO_2$ in the brain tissue are simultaneously measured in the concentration measurement apparatus 1, and the oxygen consumption amount is calculated in the calculation unit 14 and the calculation step S14, the oxygen consumption state of the brain can be monitored non-invasively and continuously by one apparatus, which is a very effective function particularly for ICU patients and patients during surgery.

Further, in the present embodiment, "filter processing of extracting a frequency component derived from respiration" refers to extracting a frequency component within a certain range including a frequency of respiration (respiratory rate), and is not limited to the case of extracting only the frequency component of respiration. Further, "extraction of a frequency component" refers to processing of reducing a magnitude of a component in a frequency range other than a frequency range including the frequency component, until the frequency component appears to the extent that the component is sufficiently identifiable, and is not limited to processing of completely removing a component in the other frequency range.

Further, in the present embodiment, obtaining the hemoglobin-related information of the "vein" means that the hemoglobin-related information mainly includes information in the vein, and does not mean that the hemoglobin-related information in the artery is not included at all. That is, the hemoglobin-related information obtained by the concentration measurement apparatus 1 and the concentration measurement method of the present embodiment may include a small amount (for example, about several %) of the contribution of the artery. Even in such a case, it can be effectively used as the hemoglobin-related information of the vein, and there is no practical problem.

As in the present embodiment, the concentration measurement apparatus 1 may include the input unit 16 for inputting filter characteristics. Similarly, the concentration measurement method of the present embodiment may include the input step S11 of inputting filter characteristics before the calculation step S14. In this case, appropriate filter characteristics according to the respiratory rate of the subject can be easily set.

As in the present embodiment, the concentration measurement apparatus 1 may include the display unit 15 for displaying the hemoglobin-related information of the vein. Similarly, the concentration measurement method of the present embodiment may include the display step S15 of displaying the hemoglobin-related information of the vein after the calculation step S14. In this case, the hemoglobin-related information of the vein can be easily shown to the measurer.

In addition, screen display in the display unit 15 will be described. (a) in FIG. 15 and (b) in FIG. 15 illustrate examples of a display screen in the display unit 15. In the display screen in (a) in FIG. 15, $\Delta O_2Hb$ and $\Delta HHb$ after the filter processing are displayed as individual graphs G31 and G32. In one example, the horizontal axis of the graphs G31 and G32 indicates time, and the vertical axis indicates a change amount.

Further, in the display screen in (b) in FIG. 15, a graph G41 representing $\Delta cHb$ after the filter processing is shown, and further, a region B22 for $\Delta O_2Hb$ and a region B23 for $\Delta HHb$ in the amplitude of the graph G41 are displayed in different colors. In one example, the horizontal axis of the graph G41 indicates time, and the vertical axis indicates a change amount. As described above, the region B22 and the region B23 are displayed in different colors, and thus, a doctor or the like can visually and intuitively recognize the ratio of oxygenated hemoglobin in veins of the measurement target portion with reference to the displayed information, and can quickly determine the state of the patient during surgery or the ICU patient.

The display unit 15 may display information such as a numerical value related to the ratio (C2/C1) of the amplitude of time change of $\Delta cHb$ (amplitude C1 shown in (b) in FIG. 15) and the amplitude of time change of $\Delta O_2Hb$ (C2 shown in (b) in FIG. 15). Further, the display unit 15 may display information such as a numerical value related to the ratio (D2/D1) of the integrated value D1 of time change of $\Delta cHb$ (sum of areas of the region B22 and the region B23 shown in (b) in FIG. 15) and the integrated value D2 of time change of $\Delta O_2Hb$ (area of the region B22 shown in (b) in FIG. 15).

By displaying any one or both of them, a doctor or the like can know the ratio of oxygenated hemoglobin in veins of the measurement target portion 51 with reference to the displayed information, and can suitably determine the state of the patient during surgery or the ICU patient. In addition, the information is calculated in the calculation unit 14 and sent to the display unit 15. Further, the information may be average values for a predetermined time (for example, 5 seconds).

As in the present embodiment, the calculation cycle of the hemoglobin-related information may be 0.5 seconds or less (10 Hz or less in terms of frequency). In general, the respiratory rate is about 10 to 60 times per minute (see Table 1). When the calculation cycle of the hemoglobin-related information is 0.5 seconds or less, the frequency component derived from respiration can be suitably extracted. In addition, the calculation cycle of the hemoglobin-related information may be changed according to the respiratory rate (or passband of the filter). In this case, the concentration measurement apparatus may further include the input unit for inputting the calculation cycle of the hemoglobin-related information, and the calculation unit may automatically change the calculation cycle of the hemoglobin-related information according to the respiratory rate (or passband of the filter).

The concentration measurement apparatus and the concentration measurement method according to the present invention are not limited to the embodiments and configuration examples described above, and various other modifications are possible. For example, in the concentration measurement apparatus 1 and the concentration measurement method of the above embodiment, $\Delta O_2Hb$, $\Delta HHb$, $\Delta cHb$, and $SvO_2$ are exemplified as the hemoglobin-related information of veins to be calculated, and further, in the concentration measurement apparatus and the concentration measurement method according to the present invention, any other hemoglobin-related information of veins may be calculated.

Further, the filter processing in the concentration measurement apparatus and the concentration measurement method according to the present invention is not limited to those exemplified in the above embodiment, and may be processing by any filter as long as it is filter processing capable of extracting a predetermined frequency component. Further, the filter processing may be any one of software processing and hardware processing.

The concentration measurement apparatus of the above embodiment is configured to include a light input unit for inputting measurement light to a measurement target portion, a light detection unit for detecting the measurement light propagated inside the measurement target portion, and generating a detection signal according to an intensity of the measurement light, and a calculation unit for obtaining hemoglobin-related information including at least one of a temporal relative change amount of a total hemoglobin concentration, a temporal relative change amount of an oxygenated hemoglobin concentration, a temporal relative change amount of a deoxygenated hemoglobin concentration, and a hemoglobin oxygen saturation based on the detection signal, and the calculation unit performs filter processing of extracting a component derived from respiration among frequency components included in the detection signal, the hemoglobin-related information, or a numerical value appearing in a calculation process of the hemoglobin-related information for obtaining the hemoglobin-related information in a vein of the measurement target portion.

The concentration measurement method of the above embodiment is configured to include a light input step of inputting measurement light to a measurement target portion, a light detection step of detecting the measurement light propagated inside the measurement target portion, and generating a detection signal according to an intensity of the measurement light, and a calculation step of obtaining hemoglobin-related information including at least one of a temporal relative change amount of a total hemoglobin concentration, a temporal relative change amount of an oxygenated hemoglobin concentration, a temporal relative change amount of a deoxygenated hemoglobin concentration, and a hemoglobin oxygen saturation based on the detection signal, and in the calculation step, filter processing of extracting a component derived from respiration among frequency components included in the detection signal, the hemoglobin-related information, or a numerical value appearing in a calculation process of the hemoglobin-related information is performed for obtaining the hemoglobin-related information in a vein of the measurement target portion.

In a certain measurement opportunity, the present inventors have observed the temporal relative change amount ($\Delta O_2Hb$) of the oxygenated hemoglobin concentration and the temporal relative change amount ($\Delta HHb$) of the deoxygenated hemoglobin concentration in detail, and have found a periodic variation that accurately coincides with the cycle of ventilation by the ventilator by chance. When a person breathes (or periodically pressurizes by a ventilator), a change in intrathoracic pressure caused by it spreads to other portions in a body, causing a change in body cavity pressure at each portion. The above pressure is exerted on the blood vessels, and the influence of the pressure is larger in the vein than in the artery, because the blood vessel wall of the artery is thick and strong whereas the blood vessel wall of the vein is thin and flexible.

It is considered that the periodic variation described above is caused by repeated expansion and contraction of the blood vessel wall of the vein due to the influence of the above pressure. Therefore, when only the periodic variation component derived from respiration is extracted from $\Delta O_2Hb$ and $\Delta HHb$, $\Delta O_2Hb$ and $\Delta HHb$ of veins can be selectively obtained. This also applies, theoretically, to other hemoglobin-related information calculated from $\Delta O_2Hb$ and $\Delta HHb$ (for example, the temporal relative change amount ($\Delta cHb$) of the total hemoglobin concentration).

In view of this, in the concentration measurement apparatus and the concentration measurement method described above, when the hemoglobin-related information is obtained based on the detection result of the measurement light propagated inside the measurement target portion, the calculation unit (in the calculation step) performs the filter processing for extracting a component derived from respiration among frequency components included in the detection signal, the hemoglobin-related information, or a numerical value appearing in a calculation process of the hemoglobin-related information. Thus, the hemoglobin-related information in the vein of the measurement target portion can be selectively obtained. Therefore, the hemoglobin-related information of veins can be obtained non-invasively using light.

The above concentration measurement apparatus may further include a display unit for displaying the hemoglobin-related information of the vein. Further, the above concentration measurement method may further include, after the calculation step, a display step of displaying the hemoglobin-related information of the vein. With this configuration, the measurer can easily check the hemoglobin-related information of the vein.

The above concentration measurement apparatus may further include an input unit for inputting information on filter characteristics of a filter in the filter processing. Further, the above concentration measurement method may further include, before the calculation step, an input step of inputting information on filter characteristics of a filter in the filter processing. With this configuration, it is possible to easily set appropriate filter characteristics (center frequency and the like) according to the respiratory rate of the subject.

In the above concentration measurement apparatus and the concentration measurement method, a filter in the filter processing may be a band-pass filter, a cutoff frequency of a low frequency side may be included in a range of 10 bpm (beat per minute) or more and 30 bpm or less, and a cutoff frequency of a high frequency side may be included in a range of 30 bpm or more and 60 bpm or less.

In general, the respiratory rate of persons decreases with age, and the respiratory rate of newborns is 30 to 60 bpm, whereas the respiratory rate of elderly persons of 80 years old or older is 10 to 30 bpm. Therefore, when the cutoff frequencies of the low frequency side and the high frequency side are set as described above, subjects of various ages from newborns to elderly persons can be handled.

In the above concentration measurement apparatus and the concentration measurement method, a filter in the filter processing may be a band-pass filter capable of selecting one passband from a plurality of passbands. In this case, an appropriate passband according to the respiratory rate of the subject can be easily set.

The above concentration measurement apparatus may further include an input unit for selecting the one passband from the plurality of passbands. Further, the above concentration measurement method may further include, before the calculation step, an input step of selecting the one passband from the plurality of passbands. In this case, an appropriate passband according to the respiratory rate of the subject can be easily selected.

Further, in the above concentration measurement apparatus and the concentration measurement method, the plurality of passbands may include a first passband including at least a range of 10 bpm or more and 20 bpm or less and a second passband including at least a range of 40 bpm or more and 50 bpm or less.

As described above, the respiratory rate of persons decreases with age, the respiratory rate of newborns is 30 to 60 bpm, whereas the respiratory rate of elderly persons of 80 years old or older is 10 to 30 bpm. Therefore, by making it possible to select the first and second passbands described above, subjects of various ages from newborns to elderly persons can be handled.

In the above concentration measurement apparatus and the concentration measurement method, a set respiratory rate of a ventilator used in combination may be included in a passband of a filter in the filter processing.

In general, the magnitude of pressurization in the ventilator is larger than the magnitude of depressurization (depth of respiration) in the spontaneous respiration, and thus, the subject using the ventilator has a large periodic variation of the hemoglobin-related information derived from respiration. Further, unlike the spontaneous respiration, the ventilation cycle of the ventilator hardly changes and is maintained constant with high accuracy. Therefore, it is easy to accurately extract only the periodic variation component derived from respiration from the hemoglobin-related information, and thus, the hemoglobin-related information of veins can be more accurately and easily obtained.

Further, the above concentration measurement apparatus may further include an input unit for receiving a signal related to the set respiratory rate from the ventilator, and the calculation unit may determine the passband of the filter in the filter processing according to the set respiratory rate. Further, the above concentration measurement method may further include, before the calculation step, an input step of receiving a signal related to the set respiratory rate from the ventilator, and in the calculation step, the passband of the filter in the filter processing may be determined according to the set respiratory rate. In these cases, the set respiratory rate of the ventilator can be easily included in the passband of the filter.

INDUSTRIAL APPLICABILITY

The embodiments can be used as a concentration measurement apparatus and a concentration measurement method capable of non-invasively obtaining hemoglobin-related information of a vein using light.

REFERENCE SIGNS LIST

1—concentration measurement apparatus, 10—main unit, 11—light emitting unit, 12—sample-hold circuit, 13—A/D conversion circuit, 14—calculation unit, 15—display unit, 141—CPU, 142—ROM, 143—RANI, 16—input unit, 17—data bus, 20—probe, 21—light input unit, 22—light detection unit, 23—holder, 24—optical fiber, 25—prism, 26—photodetection element, 27—preamplifier unit, 28—cable, 50—subject, 51—measurement target portion.

The invention claimed is:

1. A concentration measurement apparatus comprising:
a light input unit configured to input measurement light to a measurement target portion;
a light detection unit configured to detect the measurement light propagated inside the measurement target portion, and generate a detection signal according to an intensity of the measurement light;

a calculation unit configured to obtain hemoglobin-related information including at least one of a temporal relative change amount of a total hemoglobin concentration, a temporal relative change amount of an oxygenated hemoglobin concentration, a temporal relative change amount of a deoxygenated hemoglobin concentration, and a hemoglobin oxygen saturation based on the detection signal; and an input unit connected to a ventilator used in combination in a wired or wireless manner and configured to receive a signal related to a set respiratory rate from the ventilator, wherein the calculation unit is configured to perform filter processing of extracting a component derived from respiration among frequency components included in the detection signal, the hemoglobin-related information, or a numerical value appearing in a calculation process of the hemoglobin-related information for obtaining the hemoglobin-related information in a vein of the measurement target portion, the set respiratory rate of the ventilator is included in a passband of a band-pass filter in the filter processing, and the calculation unit is configured to determine the passband of the band-pass filter in the filter processing according to the set respiratory rate such that the set respiratory rate becomes a center frequency of the passband.

2. The concentration measurement apparatus according to claim 1, further comprising a display unit configured to display the hemoglobin-related information of the vein.

3. A concentration measurement method comprising:

inputting measurement light to a measurement target portion;

detecting the measurement light propagated inside the measurement target portion, and generating a detection signal according to an intensity of the measurement light;

performing a calculation of obtaining hemoglobin-related information including at least one of a temporal relative change amount of a total hemoglobin concentration, a temporal relative change amount of an oxygenated hemoglobin concentration, a temporal relative change amount of a deoxygenated hemoglobin concentration, and a hemoglobin oxygen saturation based on the detection signal; and before the calculation, receiving a signal related to a set respiratory rate from a ventilator used in combination and connected in a wired or wireless manner, wherein in the calculation, filter processing of extracting a component derived from respiration among frequency components included in the detection signal, the hemoglobin-related information, or a numerical value appearing in a calculation process of the hemoglobin-related information is performed for obtaining the hemoglobin-related information in a vein of the measurement target portion, the set respiratory rate of the ventilator is included in a passband of a band-pass filter in the filter processing, and in the calculation, the passband of the band-pass filter in the filter processing is determined according to the set respiratory rate such that the set respiratory rate becomes a center frequency of the passband.

4. The concentration measurement method according to claim 3, further comprising, after the calculation, displaying the hemoglobin-related information of the vein.

* * * * *